United States Patent [19]

Heilbron et al.

[11] Patent Number: 4,934,360
[45] Date of Patent: Jun. 19, 1990

[54] DISPOSABLE MANUAL RESUSCITATOR

[76] Inventors: Delphine R. Heilbron, 2164 Hyde St., San Francisco, Calif. 94109; Thomas L. Altshuler, 110 Hillcrest Rd., West Concord, Mass. 01742

[21] Appl. No.: 294,052

[22] Filed: Jan. 5, 1989

[51] Int. Cl.$^5$ .......................... A61M 16/08; A62B 7/00
[52] U.S. Cl. .......................... 128/205.16; 128/205.13
[58] Field of Search ............... 128/204.18, 205.13, 128/205.14, 205.16, 205.19

[56] References Cited

U.S. PATENT DOCUMENTS

| | | | |
|---|---|---|---|
| 3,106,204 | 10/1963 | Paramelle | 128/205.16 |
| 3,216,413 | 11/1965 | Arecheta Mota | 128/205.13 |
| 4,774,941 | 10/1988 | Cook | 128/205.13 |

Primary Examiner—Edgar S. Burr
Assistant Examiner—Kimberly L. Asher
Attorney, Agent, or Firm—Philip A. Dalton

[57] ABSTRACT

A manual resuscitator is disclosed which includes two disposable bellows having appropriate valves which connect via a chamber to a patient mouthpiece or face mask. The bellows are inserted into a frame comprising a manually-operated telescoping push rod and a return compression spring. When the push rod is moved upward, assisted by the return compression spring, fresh air is drawn into and stored in the inhale bellows and, simultaneously the contents of the patient's lungs are sucked into the exhaust bellows. When the push rod is pushed down, both bellows compress and, as a result, the inhale bellows forces the stored fresh air into the patient's lungs while the exhale bellows forces air plus carbon dioxide, water, smoke, etc., from the patient's lungs into the atmosphere. The inhale bellows is adapted to limit the maximum vacuum suction during exhaling. Also, the exhale bellows is adapted to limit the pressure of the fresh air forced into the patient's lungs.

6 Claims, 5 Drawing Sheets 4,934,360

DISPOSABLE MANUAL RESUSCITATOR

I. BACKGROUND OF THE INVENTION

The present invention relates to the art of resuscitation and, in particular, to a manually-operated resuscitator device.

Although mouth-to-mouth resuscitation is typically an effective technique for removing smoke, water, carbon monoxide and other foreign fluids and materials from a patient's lungs, it can be a very tiring procedure and involves the risk of transmitting communicable diseases from the person who receives the resuscitation to policemen, firemen and other administrators of the aid, and vice versa.

II. SUMMARY OF THE INVENTION

In view of the above-discussed present state of the art, it is one primary object of our present invention to provide a device that manually removes water, smoke, carbon monoxide, and other liquids and gases that a patient might have inhaled.

It is a related object of our present invention to provide a safe and effective manual device for performing resuscitation without the danger of transmitting disease to either the person receiving such resuscitation or to the person(s) administering the resuscitation.

It is another related object to provide a lightweight, portable, easily-operated manual resuscitator that avoids mouth-to-mouth contact between the recipient and the administrator of the resuscitation and in which any part contacted by patient fluids can be removed and replaced readily.

In one aspect, our resuscitator which achieves the above as well as other objectives discussed below, includes a disposable section comprising an inhale bellows and an exhaust bellows which are mounted on and communicate into a chamber, and an associated mouthpiece or face mask. The opposite ends of the two bellows are releasably mounted at spaced points along a telescopic handle, which is used to compress and expand the two bellows in unison. The two bellows contain valve assemblies at their opposite ends which cooperatively and selectively open and close to store fresh air in the inhale bellows and to suck fluid from the patient's lungs for storage in the exhaust bellows during the expansion cycle, and to force the stored fresh air into the patient's lungs and exhaust the stored patient fluids from the exhaust bellows during compression. Repetitive application of the bellows-emptying compression cycle and bellows-filling expansion cycle completely evacuates and replenishes the contents of the patient's lungs, and artificially operates the lungs.

In another aspect, discussed in greater length in the Detailed Description, the telescopic rod incorporates a compression spring which effects or assists the expansion cycle. Also, the construction of the valves is adapted to limit the fresh air pressure and the exhaust suction to which the patient is subjected.

The resuscitator can be manufactured in different sizes to more comfortably accommodate the physical size and lung capacities of infants, children and adults.

III. BRIEF DESCRIPTION OF THE DRAWINGS

The above and other aspects of our invention are disclosed in conjunction with the accompanying drawings in which.

Figure 1:
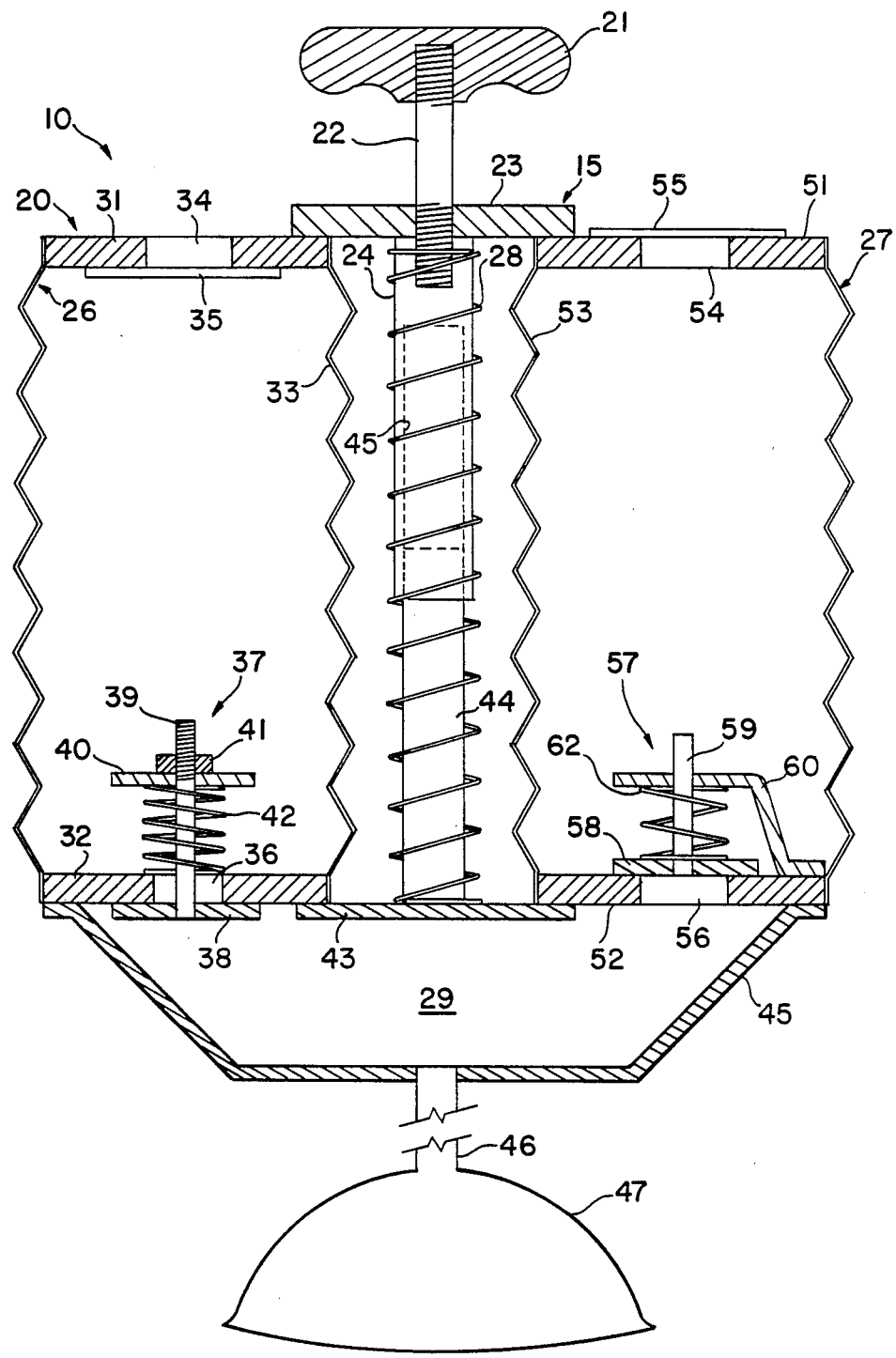
FIG. 1 is a cross-sectional view of our disposable manual resuscitator, showing the device at rest, in equilibrium, in the fully extended or expanded position.
Figure 4:
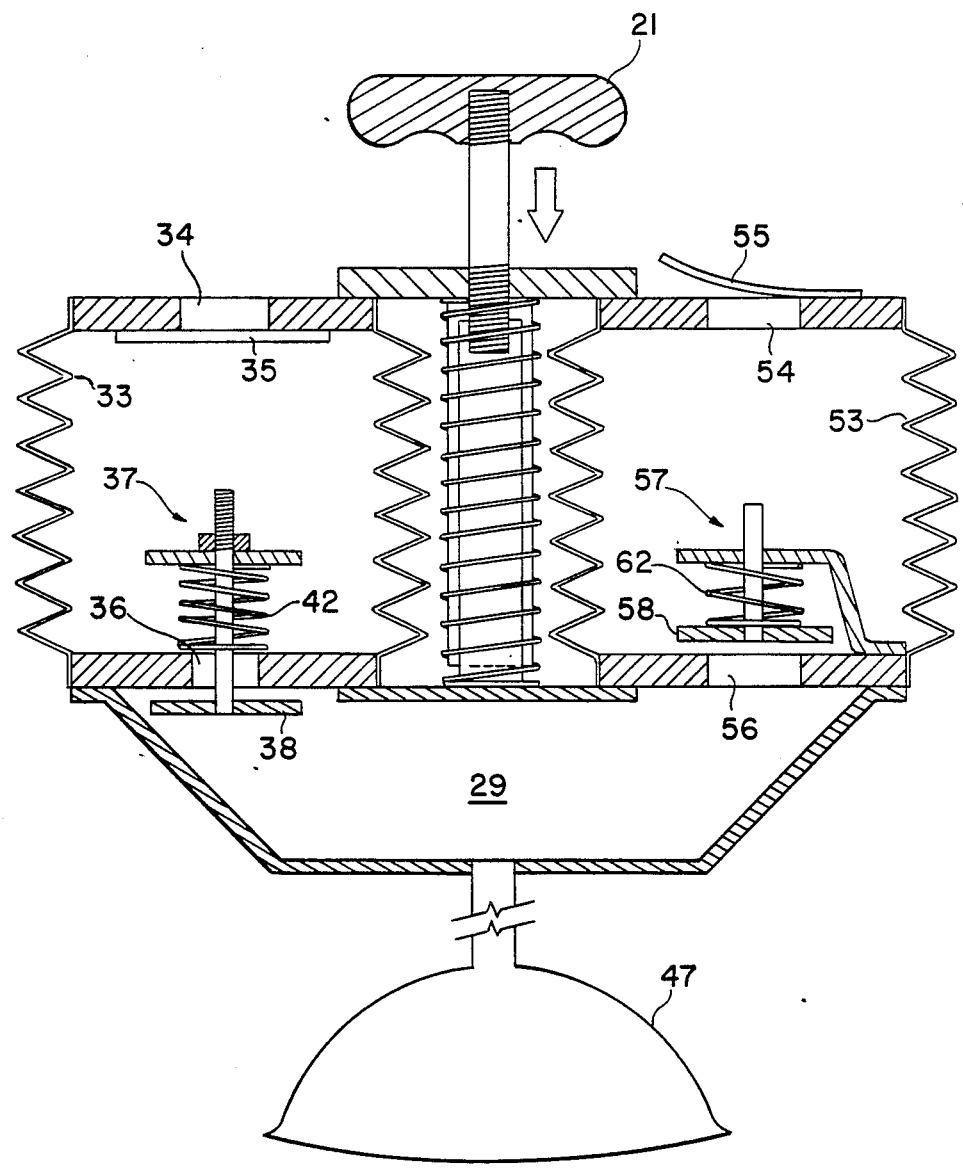
Figure 5:
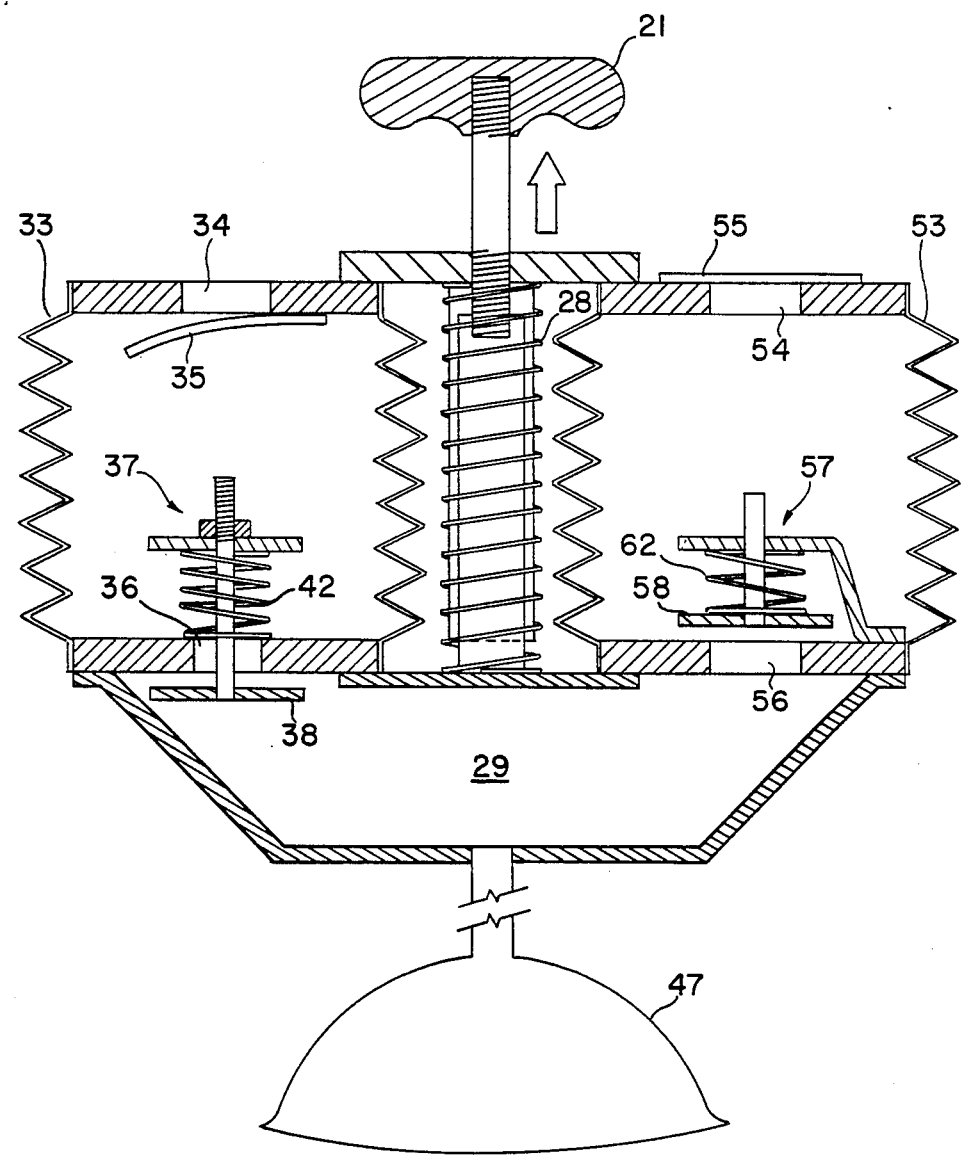

FIG. 4 is a cross-sectional view in the manner of FIG. 1 depicting inhaling operation of our resuscitator when the pressure of the fresh air applied to the mouthpiece or face mask is limited, so as not to exceed a maximum pre-determined safe pressure; and FIG. 5 is a cross-sectional view in the manner of FIG. 1 showing the exhaling operation of our resuscitator when the vacuum suction at the mouthpiece or face mask is limited, to prevent the suction from exceeding a pre-determined safe value.

IV. DESCRIPTION OF THE PREFERRED EMBODIMENT(S)

A. Construction and Overall Operation of the Disposable Manual Resuscitator

1. Separable, Disposable Construction

FIG. 1 depicts a cross-section view of a preferred embodiment of our disposable manual resuscitator, identified by the general reference numeral 10. The resuscitator 10 comprises a permanent section 15 and a readily removable, replaceable section 20 containing components which may be contacted by germ- or virus-containing fluids from the mouth, nasal passages, lungs, etc., of a patient. The disposable section 20 is mounted to the permanent section 15 in releasable fashion, as by butterfly screws (not shown), to permit ready removal and replacement by a fresh, non-contaminated section 20. Thus, subsequent handlers and operators of the resuscitator 10, as well as patients, are not exposed to infective agents contained in the fluids removed from the patient by the resuscitator.

Referring further to FIG. 1, the permanent resuscitator section 15 comprises a handle 21, mounted on a push rod 22, which itself is attached to a top plate 23. The top plate and push rod are mounted to a tube 24 which guides the motion of a fresh air (inhale) bellows assembly 26 and an exhaust (exhale) bellows assembly 27 during associated expansion and contraction strokes. Tube 24 also supports a circumferential compression return spring 28 which, preferably, is made of stainless steel or other moisture-proof material.

The disposable bellows section 20 comprises the inhale bellows assembly 26; the exhale bellows assembly 27; chamber 29 formed by a cup-shaped lower wall 45 and an upper wall formed in combination by the support plate 43 for the bellows assemblies and the bottom plates 32 and 52 of the bellows assemblies tube 46 and mouthpiece 47. Both bellows assemblies are mounted between the top support plate 23 and the bottom support plate 43 A cylindrical lower rod 44 is attached to the upper surface of the bottom support plate 43 and fits within a bore 45 in the top tube 24, permitting telescopic extension and contraction of the two tube assembly. Rod 44 also acts as a guide for the bellows and for the spring 24, and prevents the bellows from closing too far, thus preventing damage to the bottom valve assemblies 37 and 57.

As described below, the two bellows assemblies are constructed so that they communicate with the interior of the chamber 29 and the ambient atmosphere for alternately extracting fluids (including, but not limited to, water, carbon dioxide-containing air and smoke-containing air) from a patient's lungs and replacing the fluid with fresh air.

2. Construction and Operation of the Inhale Bellows Assembly

Figure 2:
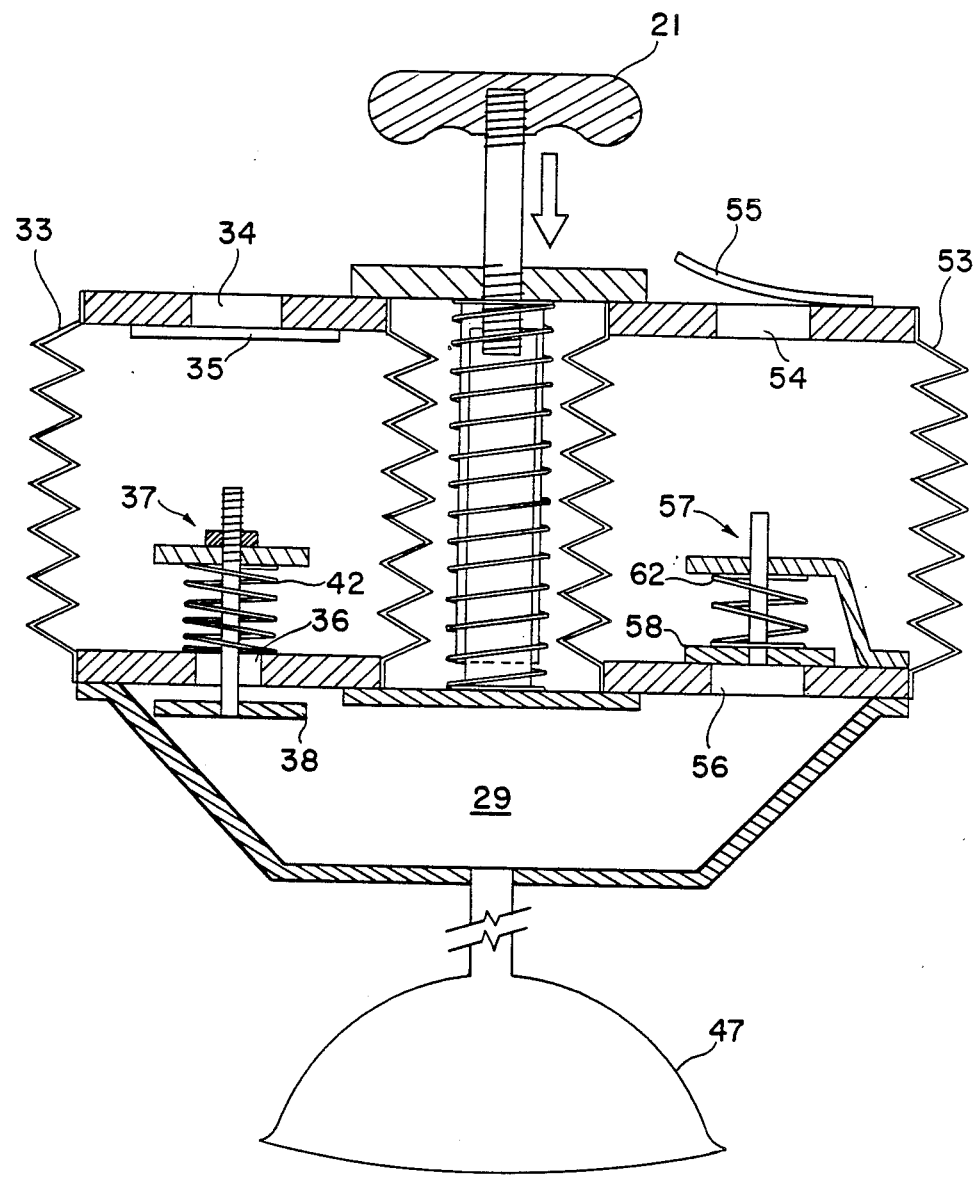
FIG. 2 is a cross-sectional view in the manner of FIG. 1 showing the operation of our resuscitator during the bellows-emptying compression cycle.

The fresh air or inhale bellows assembly 26 includes a bellows 33 that is mounted between an apertured top plate 31, and an apertured bottom plate 32. The top bellows plate 31 is mounted to the top support plate 23, as by quick-release butterfly screws or the like and, preferably, the bottom bellows plate 32 is permanently joined to the chamber 29 at bottom support plate 43. Separate, normally closed (N.C.) valve means 35 and 37 cover the top, inlet hole or port 34 and the bottom outlet hole or port 36, and are designed, respectively, to open during expansion (FIG. 3) and compression (FIG. 2) of the bellows, to alternately fill the fresh air bellows 33 with fresh air (FIG. 3) and then force the fresh air into the patient's lungs (FIG. 2).

Preferably, the fresh air inlet valve means 35 is a simple resilient flap attached to the bottom side of the bellows top plate 31.

Preferably, fresh air outlet valve means 37 is a spring-loaded valve assembly comprising a valve 38 mounted on and positioned by a valve stem 39 (which passes through the hole 36) on the chamber 29 side of the bottom plate 32. A compression spring 42 is mounted on the valve stem 39 between the bottom plate 32 and a disk 40 that is retained on the valve stem by an adjustable lock nut 41. Adjusting the position of the lock nut along the valve stem causes the spring 42 to bias the valve 38 closed over the hole 36 with pre-selected force.

Figure 3:
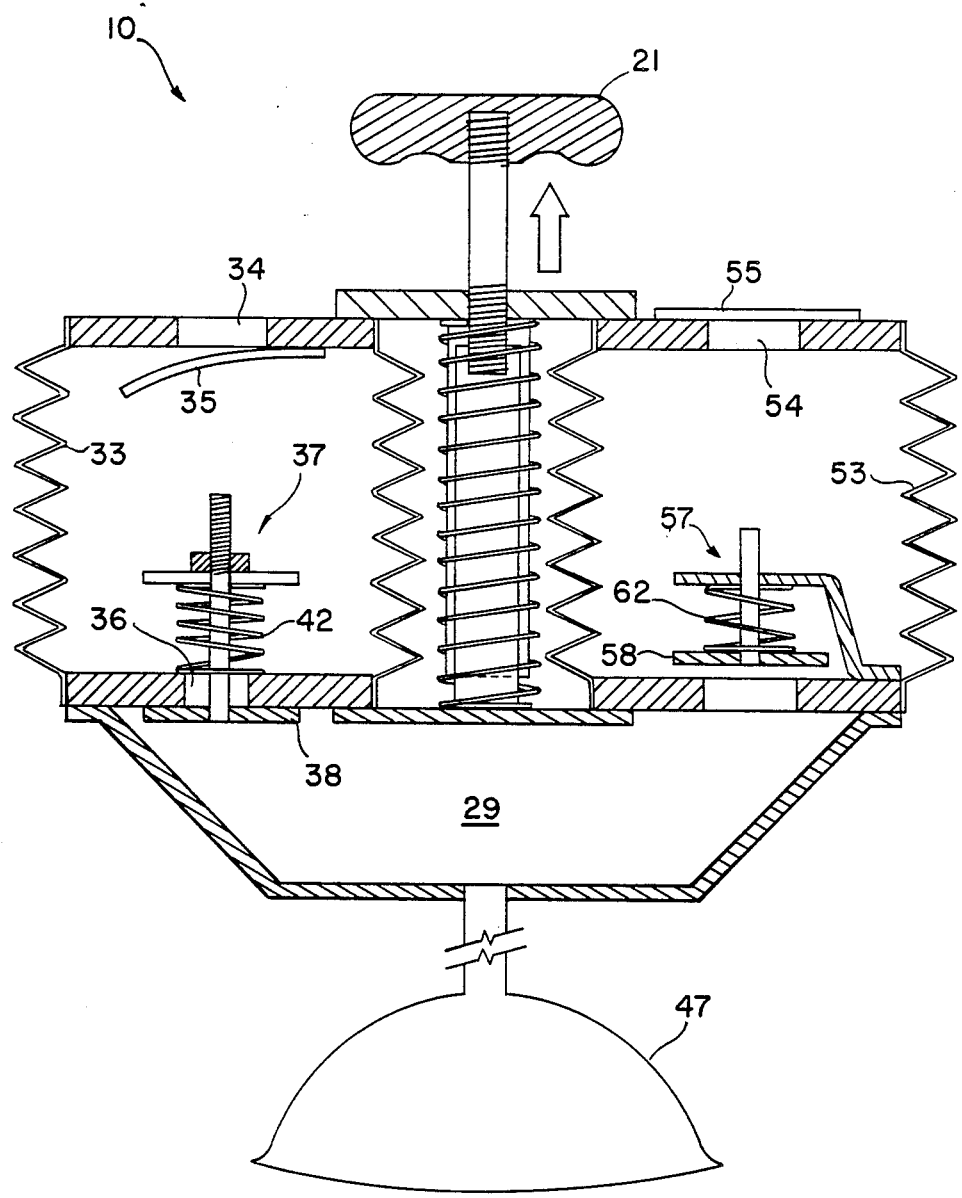
FIG. 3 is a cross-sectional view in the manner of FIG. 1 showing the operation of our resuscitator during the bellows-filling expansion cycle.

Referring to FIG. 3 and assuming that the mouthpiece or face mask 47 is placed over a patient's nose and mouth, during bellows-filling expansion of the resuscitator 10 the action of the compression spring 28 alone, or the combination of the compression spring force and manually pulling the handle 21, expands the bellows 33 from an initially compressed state. The resulting decreased internal bellows pressure relative to that of the ambient atmosphere and that in the chamber 29 (1) maintains the valve 38 N.C. against the plate 32, but (2) bends flap 35 inwardly, opening the inlet hole 34 so that fresh air rushes into the low pressure bellows 33. When the expanding movement of the bellows is stopped and the pressure is equalized, flap 35 closes, sealing the fresh air-filled bellows 33.

Conversely, and referring to FIG. 2, when handle 21 is pushed downwardly, compressing the bellows 33, the inlet flap 35 is maintained in or returned to its N.C. position against the inside of the plate 31 by the increasing internal bellows pressure, which also overcomes the preset biasing action of the spring 42 and forces open the valve 38. As a consequence, the fresh air in the bellows 33 is forced through the hole 36 and into the patient's nose and mouth via the chamber 29 and mouthpiece 47.

3. Construction and Operation of the Exhaust Bellows Assembly

Similar to the fresh air bellows assembly 26, the exhaust bellows assembly 27 comprises a bellows 53 that is mounted between apertured top and bottom plates 51 and 52 mounted to the support plates 23 and 43. Exhaust hole or port 54 in the top bellows plate 51 is covered by a flexible exhaust outlet flap 55 mounted on the outside of the plate. A spring-loaded exhaust inlet valve assembly 57 comprises a valve 58 mounted on and positioned by a valve stem 59 on the bellows side of the bottom plate 52. A compression spring 62 is mounted over the valve stem 59 between the bottom plate 52 and an angled bracket 60, which is bonded or otherwise mounted to the bottom plate 52.

Referring to FIG. 2, during bellows-emptying compression of the resuscitator 10, the exhaust valve 58 is retained in its normally closed position over the exhaust inlet hole 56 by the increasing pressure within the bellows 53. The increased pressure also opens normally closed exhaust outlet flap 55 outwardly so that the fluid captured within the bellows 53 from the patient's lungs is exhausted under pressure to the ambient.

Conversely, and referring to FIG. 3, when the resuscitator 10 is expanded, the decreasing pressure within the expanding internal volume of the bellows 53, (1) draws the outlet flap 55 inwardly, keeping it closed over outlet hole 54, and (2) overcomes the pre-selected biasing force exerted by spring 62 and draws valve 58 inwardly, opening the inlet hole 56 and sucking fluid from the patient's lungs via the chamber 29 into the bellows 53. When expansion of the bellows is stopped, valve 58 closes, temporarily sealing the fluid within the bellows 53 for subsequent exhaling during the next compression stroke (FIG. 2).

B. Exemplary Overall Operation Cycle

In the previous section, the individual operation of the fresh air (inhale) and exhaust (exhale) bellows assemblies was discussed. This section emphasizes the combined cooperative operation of the two bellows assemblies.

As mentioned previously, during use of our disposable manual resuscitator 10, the mouthpiece or face mask 47 is positioned over the patient's mouth and nose preparatory to alternately forcing fresh air into the patient's lungs (the compression or inhale cycle) and extracting or sucking air or other fluids such as water or smoke from the lungs (the exhale cycle).

To initiate the bellows-emptying inhale cycle, and referring again to FIG. 2, when the handle 21 is pushed to compress the bellows assemblies, the increasing pressure in the fresh air bellows 33 opens the fresh air outlet valve means 37, while keeping closed the fresh air intake valve means 35, so that the fresh air from the bellows is forced into the patient's lungs. At the same time, the exhaust inlet valve means 57 in the exhaust bellows 53 closes/stays closed, because the spring 62 has sufficient force to overcome the increasing air pressure in chamber 29 due to the incoming air from the inhale bellows 33. Also, the increasing internal exhaust bellows pressure opens exhaust outlet valve means 55 and exhausts any fluid previously stored in the exhaust bellows 53 to the ambient.

Referring now to FIG. 3, when the handle 21 is released or when it is pulled upwardly, the spring 28 (alone or in combination with the manual pulling on the handle 21) forces the two bellows assemblies to expand, thereby decreasing the internal bellows pressure. The fresh air outlet valve means 37 closes, while the fresh air intake valve means 35 opens, allowing fresh air to be sucked into the inhale bellows 33. At the same time, the exhaust outlet valve means 55 is closed by the vacuum within the exhaust bellows. Also, the exhaust intake valve means 57 opens, because the pressure difference between the vacuum within the exhaust bellows 53 and the pressure within chamber 29 overcomes the force of the spring 62, which tries to keep valve 57 closed. The opening of valve 57 allows fluid from the patient's lungs to be sucked into the exhaust bellows 53. When the expansion of the resuscitator stops and the pressure differential decreases, the valve 57 closes, storing the fluid from the patient's lungs in the exhaust bellows 53, and the valve 35 closes, storing fresh air in the inhale bellows 33, both preparatory to the next cycle of bellows-emptying compression and bellows-filling expansion.

Referring to FIG. 4, the biasing force of spring 62 is selected so that were the pressure within the fresh air bellows 33 to exceed a safe level during the inhale cycle, the increased pressure within the chamber 29 would overcome the force of the spring 62 and open the valve 57, in addition to valve 55, thereby venting the excess pressure to atmosphere. This operation prevents possible damage to the patient's lungs from excessive inhalation pressure.

Referring to FIG. 5, if, during the exhale cycle, the vacuum within the chamber 29 becomes too great for safety, the valve 37 opens, communicating fresh air from the inhale bellows 33 into the chamber 29 and reducing the pressure there. This operation prevents damage to the patient's lungs resulting from excessive exhaust suction.

Please note, the biasing force of springs 42 and 62 and the pressure differential which actuates the above safety venting operations are determined by the strength of the spring (the spring constant) and the compression of the spring.

Preferably the bellows are made of transparent plastic or other lightweight liquid-impervious material to enable the operator of the equipment to observe the operation of the bottom intake and exhaust valves.

Thus, it will be seen that the objects set forth above, among those made apparent from the preceding description, are efficiently attained and, since certain changes may be made in the above construction without departing from the scope of the invention, it is intended that all matter contained in the above description or shown in the accompanying drawings shall be interpreted as illustrative and not in a limiting sense.

I claim:

1. A resuscitator, comprising:
    a first permanent section (15) comprising: a telescoping rod assembly (24, 44) having a gripping handle (21) at one end; top and bottom support plates (23, 43) mounted at spaced first and second points on the rod assembly for relative movement toward and away from one another during telescoping movement of the rod assembly; and a compression spring (28) mounted along the rod assembly between the plates (23, 43) for normally biasing the rod assembly in an extended position;
    a second disposable section (20) attached to the first section (15) and comprising: collapsible inhale and exhaust bellows assemblies (26, 27) mounted on opposite sides of the rod assembly (24, 44) to and between the top and bottom support plates (23, 43), for collapsing and expanding during inward and outward movement of the rod assembly, both bellows assemblies having holes (34, 54; 36, 56) in top and bottom ends thereof; a mouthpiece (47); and a chamber (29) communicating with the bottom holes (36, 56) in the bellows assemblies and with the mouthpiece (47) for communicating fresh air from the inhale bellows assembly (26) to the patient during compression and for sucking fluid from a patient's lungs into the exhaust bellows assembly (27) during expansion;
    said inhale bellows assembly (26) including: a first, normally closed fresh air inlet valve means (35) mounted covering the top hole (34) thereof, said fresh air inlet valve means opening during expansion of the bellows to draw fresh air into the inhale bellows; and a second, normally closed fresh air outlet valve means (37) mounted covering the bottom hole (36) thereof, said fresh air outlet valve means opening during compression of the bellows assembly for supplying stored fresh air under positive pressure to the patient;
    said exhaust bellows assembly (27) including: a third, normally closed exhaust inlet valve means (57) mounted covering the bottom hole (56) thereof, said exhaust inlet valve means opening during expansion of the bellows for sucking fluid from the patient's lungs into the exhaust bellows; and a fourth, normally closed exhaust outlet valve means (55) mounted covering the top hole (54) thereof, said outlet valve means opening during compression of the exhaust bellows assembly for exhausting fluid therein to the assembly;
    the second disposal section, including the inhale and exhaust bellows assemblies (26, 27), being releasably attached to the top support plate (23) for detachment from the first permanent section including the handle, so that resuscitator components contacted by patient fluids, including the two bellows assemblies (26, 27), the chamber (29) and the mouthpiece (47), can be detached from the handle and rod and replaced.

2. The resuscitator of claim 1, wherein (1) the inhale bellows assembly (26) further comprises an elongated bellows (33) mounted at top and bottom ends thereof to top and bottom end plates (31, 32) which have the top and bottom holes (34, 36) formed therein; and (2) the bottom, fresh air outlet valve means (37) comprises: a valve stem (39) extending through the outlet hole (36) in the bottom end plate (32) thereof and mounting a valve (38) on the chamber side of the plate; a disk (40) on the section of the valve stem extending into the bellows; a compression spring (42) on the valve stem between the disk and the plate; and lock means (41) attached to the valve stem behind the disk for adjusting the position of the disk along the valve stem and thereby selecting a compressive force exerted by the spring sufficient to maintain the valve (38) in a normally closed position against the plate (32) which is overcome by increased internal pressure during compression and the resulting pressure difference between the inhale bellows (33) and the chamber (29), to force the bellows contents under pressure into the patient's lungs.

3. The resuscitator of claim 2, wherein the spring force is selected such that if, during the expansion cycle, the vacuum suction in the chamber (29) reaches a predetermined value, the pressure differential between the inhale bellows (33) and the chamber opens the bottom, fresh air outlet valve (37), to relieve the vacuum suction in the chamber.

4. The resuscitator of claim 1, wherein (1) the exhaust bellows assembly (27) further comprises an elongated bellows (53) mounted at top and bottom ends thereof to top and bottom end plates (51, 52) which have the top and bottom holes (54, 56) formed therein; and (2) the bottom, exhaust inlet valve means (57) comprises: a valve stem (59); a bracket (60) extending over the bottom, inlet hole (56) and having a hole therein receiving the valve stem; a valve (58) mounted on the valve stem inside the exhaust bellows and proximate the bottom, inlet hole; a compression spring (62) between the bracket and the valve urging the valve normally closed against the bottom end plate (52) with a pre-selected force, said force being overcome by decreased internal pressure within the exhaust bellows (53) during the expansion cycle and the resulting pressure difference between the exhaust bellows and the chamber (29), to suck the contents of the patient's lungs into the exhaust bellows.

5. The resuscitator of claim 4, wherein the spring force is selected such that if, during the compression cycle, the pressure in the chamber (29) reaches a predetermined value, the pressure difference between the chamber and the exhaust bellows (53) opens the bottom, exhaust inlet valve (57), thereby venting the pressure in the inhale bellows and the chamber.

6. The resuscitator of any one of claims 1-5, wherein the bellows (33, 53) are made of transparent material to permit observation of the condition of the internal bellows and the valve means therein.

* * * * *